United States Patent [19]
Booth et al.

[11] Patent Number: 5,518,000
[45] Date of Patent: May 21, 1996

[54] OSCILLOMETRIC BLOOD PRESSURE MONITOR EMPLOYING DEFLATION PERIODS OF ALTERNATING DURATIONS

[75] Inventors: John Booth; Richard Medero, both of Tampa, Fla.

[73] Assignee: Johnson & Johnson Medical, Inc., New Brunswick, N.J.

[21] Appl. No.: 315,867

[22] Filed: Sep. 30, 1994

[51] Int. Cl.⁶ .................................................. A61B 5/00
[52] U.S. Cl. ........................... 128/680; 128/681; 128/682
[58] Field of Search .............................. 128/677, 680–3, 128/687

[56] References Cited

U.S. PATENT DOCUMENTS

| | | | |
|---|---|---|---|
| 4,349,034 | 9/1982 | Ramsey, III | 128/681 |
| 4,360,029 | 11/1982 | Ramsey, III | 128/681 |
| 4,461,266 | 7/1984 | Hood, Jr. et al. | 128/681 |
| 4,543,962 | 10/1985 | Medero et al. | 128/682 |
| 4,546,775 | 10/1985 | Medero | 128/681 |
| 4,627,440 | 12/1986 | Ramsey, III et al. | 128/682 |
| 4,638,810 | 1/1987 | Ramsey, III et al. | 128/681 |
| 4,754,761 | 7/1988 | Ramsey, III et al. | 128/683 |
| 4,774,960 | 10/1988 | Arnold et al. | 128/681 |
| 4,889,133 | 12/1989 | Nelson et al. | 128/681 |
| 4,926,873 | 5/1990 | Frankenreiter | 128/681 |
| 4,949,710 | 8/1990 | Dorsett et al. | 128/680 |
| 4,984,577 | 1/1991 | Frankenreiter | 128/681 |
| 5,052,397 | 10/1991 | Ramsey, III et al. | 128/682 |
| 5,054,495 | 10/1991 | Uemura et al. | 128/680 |
| 5,103,833 | 4/1992 | Apple | 128/687 |
| 5,170,795 | 12/1992 | Ramsey, III et al. | 128/682 |
| 5,215,096 | 6/1993 | Zapf et al. | 128/680 |
| 5,218,968 | 6/1993 | Apple | 128/687 |
| 5,253,648 | 10/1993 | Walloch | 128/681 |
| 5,261,413 | 11/1993 | Kawahara | 128/682 |
| 5,280,790 | 1/1994 | Brooks | 128/681 |
| 5,311,872 | 5/1994 | Apple | 128/687 |
| 5,427,109 | 6/1995 | Frankenreiter | 128/681 |

*Primary Examiner*—Angela D. Sykes
*Assistant Examiner*—Robert L. Nasser
*Attorney, Agent, or Firm*—Woodcock Washburn Kurtz Mackiewicz & Norris

[57] ABSTRACT

An automated sphygmomanometer in which the timeout duration of respective deflation periods during which oscillatory complexes may be detected is alternated so that the monitor cannot synchronize with the heart rate for more than one deflation step. The timeout durations at each deflation step are alternated to have long-short-long-short durations so that the overall duration of the measurement cycle is preferably about the same as in conventional monitors in which the timeout periods all have the same duration. Once the oscillatory complexes are detected, the timeout is typically not needed and the processing proceeds to the next deflation step in a conventional manner.

6 Claims, 4 Drawing Sheets

OSCILLOMETRIC BLOOD PRESSURE MONITOR EMPLOYING DEFLATION PERIODS OF ALTERNATING DURATIONS

FIELD OF THE INVENTION

This invention relates to automated blood pressure monitoring, and more particularly, to automated blood pressure monitors that utilize a pneumatic cuff for accomplishing a sphygmomanometric measurement on a patient.

BACKGROUND OF THE INVENTION

The sphygmomanometric class of automated blood pressure monitors employs an inflatable cuff to exert controlled counter-pressure on the vasculature of a patient. One large class of such monitors, exemplified by that described in U.S. Pat. Nos. 4,349,034 and 4,360,029, both to Maynard Ramsey, III and commonly assigned herewith, employs the oscillometric methodology. In accordance with the Ramsey patents, an inflatable cuff is suitably located on the limb of a patient and is pumped up to a predetermined pressure above the systolic pressure. Then, the cuff pressure is reduced in predetermined decrements, and at each level, pressure fluctuations are monitored. The resultant signals typically consist of a DC voltage with a small superimposed variational component caused by arterial blood pressure pulsations (referred to herein as "oscillatory complexes" or just simply "oscillations"). After suitable filtering to reject the DC component and to provide amplification, peak pulse amplitudes (PPA) above a given base-line are measured and stored. As the decrementing continues, the peak amplitudes will normally increase from a lower level to a relative maximum, and thereafter will decrease. The lowest cuff pressure at which the oscillations have a maximum value has been found to be representative of the mean arterial pressure ("MAP"). Systolic and diastolic pressures can be derived either as predetermined fractions of MAP, or by more sophisticated methods of direct processing of the oscillatory complexes.

The step deflation technique as set forth in the Ramsey patents is the commercial standard of operation. A large percentage of clinically acceptable automated blood pressure monitors utilize the step deflation rationale. Accordingly, many subsequent developments have been directed at minimizing the duration of this step deflation period so as to minimize patient discomfort. For example, in U.S. Pat. No. 4,926,873 to Frankenreiter, the size of the deflation steps for a measurement cycle is varied from measurement to measurement as a function of the patient's actual blood pressure as measured in the preceding measuring cycle. This allows the duration of the measurement cycle to be minimized since extra steps can be avoided for patients with hypertension and more accurate measurements can be made for patients with hypotension. However, the duration of each deflation step within a particular measurement cycle is not varied.

On the other hand, in U.S. Pat. No. 4,543,962 to Medero et al., U.S. Pat. No. 4,889,133 to Nelson et al., and U.S. Pat. No. 4,949,710 to Dorsett et al., signal processing techniques are used to minimize the duration of each deflation step within a particular measurement cycle needed for detecting and processing the oscillatory complexes. However, such systems typically use a fixed "timeout" period at each pressure level to search for the oscillatory complexes and only advance to the next step when one or more suitable oscillatory complexes are detected or the "timeout" is reached. Unfortunately, if a patient's heart rate has the same periodicity as the deflates and the oscillatory complexes occur during the deflate interval, it is possible that the monitor will not find any oscillatory complexes during the fixed search period and that several steps of oscillatory complexes will be missed. Moreover, if the systolic level is missed as a result, the pressure cuff would be re-pumped to a much higher pressure, thereby causing unnecessary discomfort to the patient.

One solution to the afore-mentioned problem is to extend the deflation period to some time greater than the maximum duration expected between oscillatory complexes so that an oscillatory complex will always be obtained during a deflate step. However, such a solution would cause the blood pressure determination time to be undesirably extended since the monitor would take longer to step down from the initial inflation pressure to the pressure where the complexes are large enough to be measured for the MAP determination.

It is, accordingly, a primary object of the present invention to minimize the possibility that oscillatory complexes will occur during cuff deflation and thus be missed by the detection circuitry.

It is a further object of the present invention to enable oscillatory complexes to be detected in each deflation step without extending the overall duration of the blood pressure measurement period.

It is also an object of the present invention to prevent the systolic pressure from being missed by the detection circuitry so that the cuff is not re-pumped to an uncomfortably high pressure.

SUMMARY OF THE INVENTION

The above objects have been met in accordance with the present invention by providing an automated sphygmomanometer in which the timeout period of respective deflation measurement periods is alternated so that the monitor cannot synchronize with the heart rate for more than one deflation step. Preferably, the detection periods at each deflation step are alternated to have long-short-long-short durations so that the overall duration of the measurement cycle is the same as in conventional monitors in which the detection periods all have the same duration. In other words, the timeout period during which oscillatory complexes may be detected is alternatingly varied in duration for respective deflation steps. Of course, once the oscillatory complexes are detected, the timeout is typically not needed and the processing may proceed to the next deflation step in a conventional manner.

BRIEF DESCRIPTION OF THE DRAWINGS

The present invention will be better understood after reading the following detailed description of the presently preferred embodiments thereof with reference to the appended drawings, in which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 1-4. Those skilled in the art will readily appreciate that the description given herein with respect to those figures is for explanatory purposes only and is not intended in any way to limit the scope of the invention. Accordingly, all questions regarding the scope of the invention should be resolved by referring to the appended claims.

In U.S. Pat. No. 4,360,029, Ramsey discloses in great detail a system for oscillometric blood pressure monitoring to which the principles of the present invention may be applied with advantage. The disclosure of the Ramsey '029 patent is incorporated by reference herein. The following description of FIG. 1 will act as a brief summary of the operation of that system.

Figure 1:
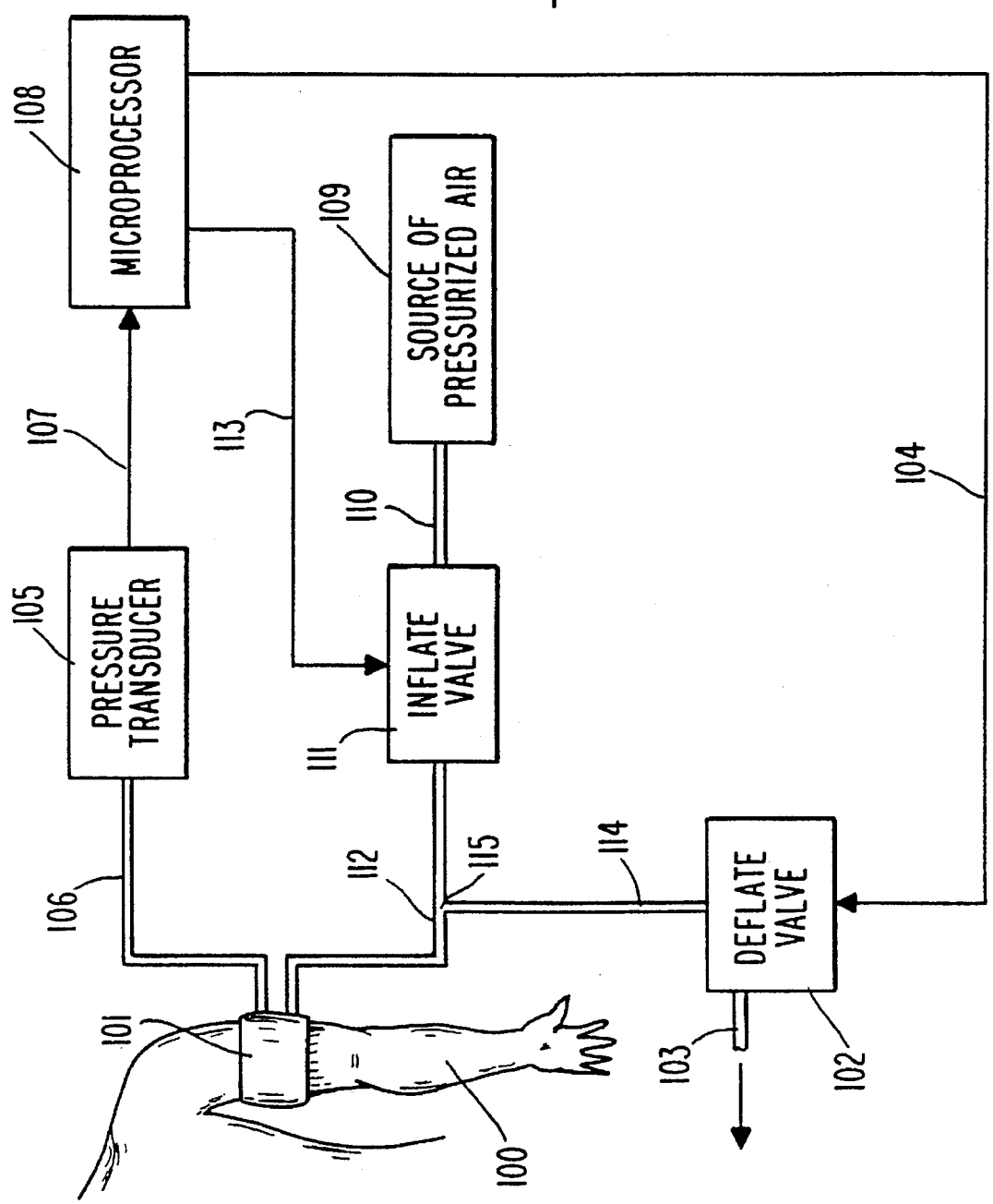
FIG. 1 is a schematic representation of a blood pressure monitor embodying the present invention.

In FIG. 1, the arm 100 of a human subject is shown wearing a conventional flexible inflatable and deflatable cuff 101 for occluding the brachial artery when fully inflated. As the cuff 101 is deflated using deflate valve 102 having exhaust 103, the arterial occlusion is gradually relieved. As will be described more fully below, the deflation of cuff 101 via deflate valve 102 is controlled by a microprocessor via a control line 104.

A pressure transducer 105 is coupled by a duct 106 to the cuff 101 for sensing the pressure therein. In accordance with conventional oscillometric techniques, pressure oscillations in the artery are sensed by changes in the counter-pressure of the cuff 101, and these pressure oscillations are converted into an electrical signal by transducer 105 and coupled over path 107 to a microprocessor 108 for processing. In addition, a source of pressurized air 109 is connected via a duct 110 through an inflate valve 111 and a duct 112 to the pressure cuff 101. The inflate valve 111 is electrically controlled through a connection 113 from the microprocessor 108. Finally, the deflate valve 102 is connected by duct 114 via a branch connection 115 with the duct 112 leading to cuff 101.

From the standpoint of the principles of the present invention, the processing of the signals from pressure transducer 105 by the microprocessor 108 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al. in U.S. Pat. No. 4,543,962, of Medero in U.S. Pat. No. 4,546,775, of Hood, Jr. et al. in U.S. Pat. No. 4,461,266, of Ramsey, III et al. in U.S. Pat. No. 4,638,810, of Ramsey, III et al. in U.S. Pat. No. 4,754,761, of Ramsey, III et al. in U.S. Pat. No. 5,170,795, and of Ramsey, III et al. in U.S. Pat. No. 5,052,397, all of which are commonly assigned herewith and the disclosures of which are hereby incorporated by reference. In any event, it is desirable to use any of the known techniques to determine the quality of the oscillatory complexes received at each level so that the blood pressure determination is made using actual blood pressure data and not artifacts.

The apparatus described above with reference to FIG. 1, except for the programming of the microprocessor 108, can be substantially the same as that disclosed in the Ramsey, III et al. '029 and '034 patents. Thus, during operation of the apparatus illustrated in FIG. 1, it can be assumed that air under pressure to about 8–10 p.s.i. is available in the source of pressurized air 109. When it is desired to initiate a determination of blood pressure, the microprocessor 108 furnishes a signal over path 113 to open the inflate valve 111. The deflate valve 102 is closed. Air from the source 109 is communicated through inflate valve 111 and duct 112 to inflate the cuff 101 to a desired level, preferably above the estimated systolic pressure of the patient. Microprocessor 108 responds to a signal on path 107 from the pressure transducer 105, which is indicative of the instantaneous pressure in the cuff 101, to interrupt the inflation of the cuff 101 when the pressure in the cuff 101 reaches a predetermined value above the estimated systolic pressure of the patient. Such interruption is accomplished by sending a signal over path 113 instructing inflate valve 111 to close. Once inflate valve 111 has been closed, the blood pressure measurement can be obtained by commencing the deflate routine.

As noted above, actual measurement of the blood pressure under the control of the microprocessor 108 and the deflate valve 102 and as sensed by pressure transducer 105 can be accomplished in any suitable manner such as that disclosed in the aforementioned patents. At the completion of each measurement cycle, the deflate valve 102 can be re-opened long enough to relax the cuff pressure substantially completely via exhaust 103. Thereafter, the deflate valve 102 is closed for the start of a new measurement cycle.

By way of a summation, when a blood pressure measurement is desired, the inflate valve 111 is opened while the cuff pressure is supervised by pressure transducer 105 until the cuff pressure reaches the desired level. The inflate valve 111 is then closed. Thereafter, the deflate valve 102 is operated using signal 104 from microprocessor 108 and the blood pressure measurement taken. To this point, the monitor operates in a conventional manner. The present invention relates to a modification of the deflation phase, and that operation will now be described with particular reference to FIGS. 2–4.

Figure 2:
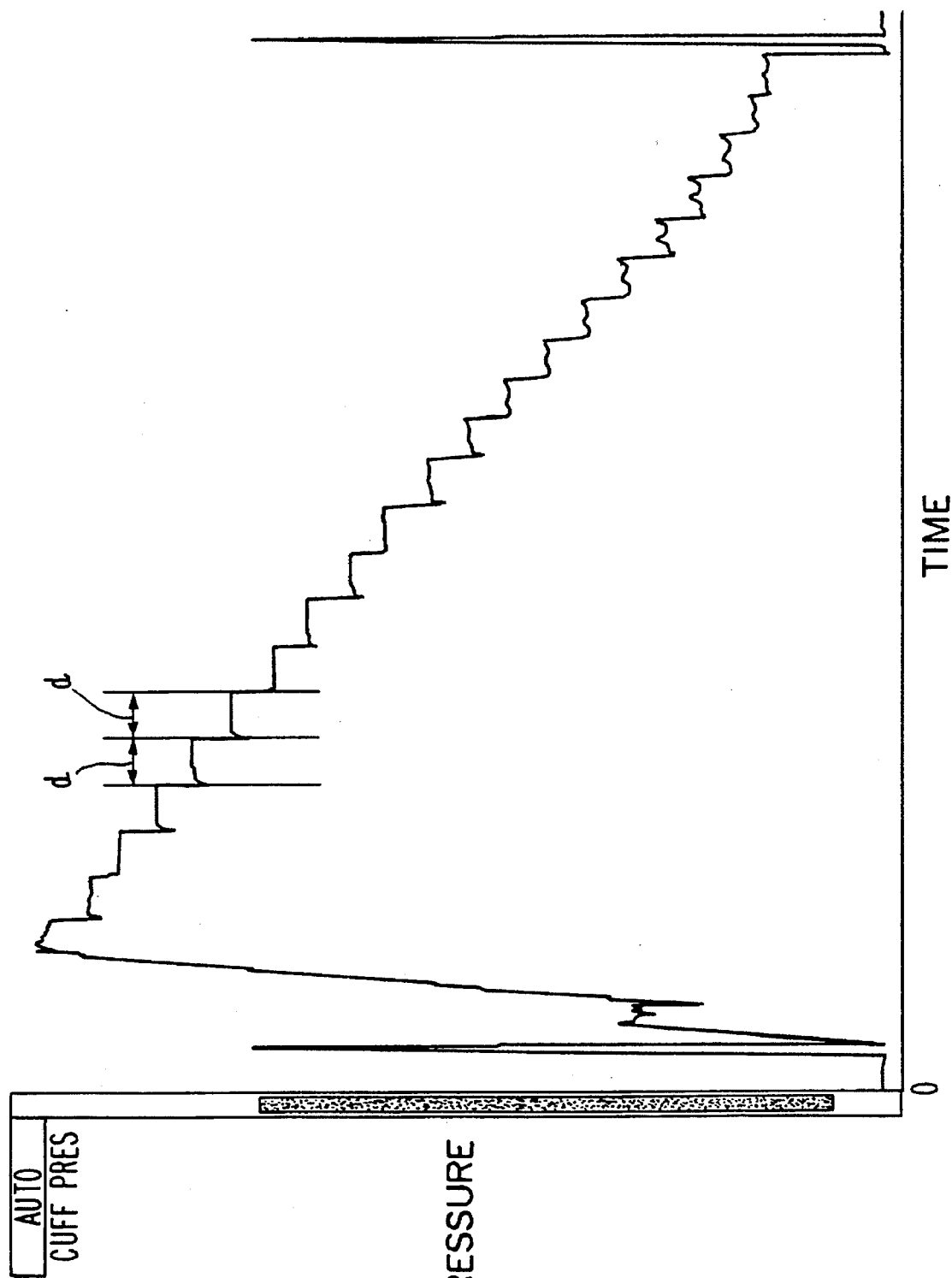
FIG. 2 is a pressure versus time graph illustrating a measuring cycle including step deflation steps as in a conventional noninvasive blood pressure measurement system.

In typical automatic sphygmomanometric devices, the cuff deflation operation is accomplished in equal decrements, usually about 8 mm Hg per step. Prior art FIG. 2 illustrates a pressure versus time graph illustrating a conventional cuff step deflation and measurement cycle for a conventional noninvasive blood pressure monitor. As illustrated, the cuff 101 is inflated to a pressure above the systolic pressure, and the cuff 101 is then deflated in steps of equal duration of about 8 mm Hg per step. A timeout duration d is provided at each step during which the signal processing circuitry searches for oscillatory complexes in accordance with the techniques described in the afore-mentioned patents. At the end of timeout duration d, the cuff pressure is decremented even if no oscillatory complex is detected.

As noted above, it is possible that no oscillatory complex is detected during a particular deflation step because the oscillatory complex occurred during the time period that the cuff 101 is deflated and no detection is being performed. Indeed, it is possible that a patient's heart rate may have the same period d as the timeout period and that the oscillatory complexes will occur during several consecutive deflate intervals. As a result of this synchronization, several steps of complex data will be missed by the pressure transducer 105. For example, if d= 1 sec., a heart rate of 60 beats per minute which is synchronized with the deflate interval would not be detected by pressure transducer 105.

Figure 3:
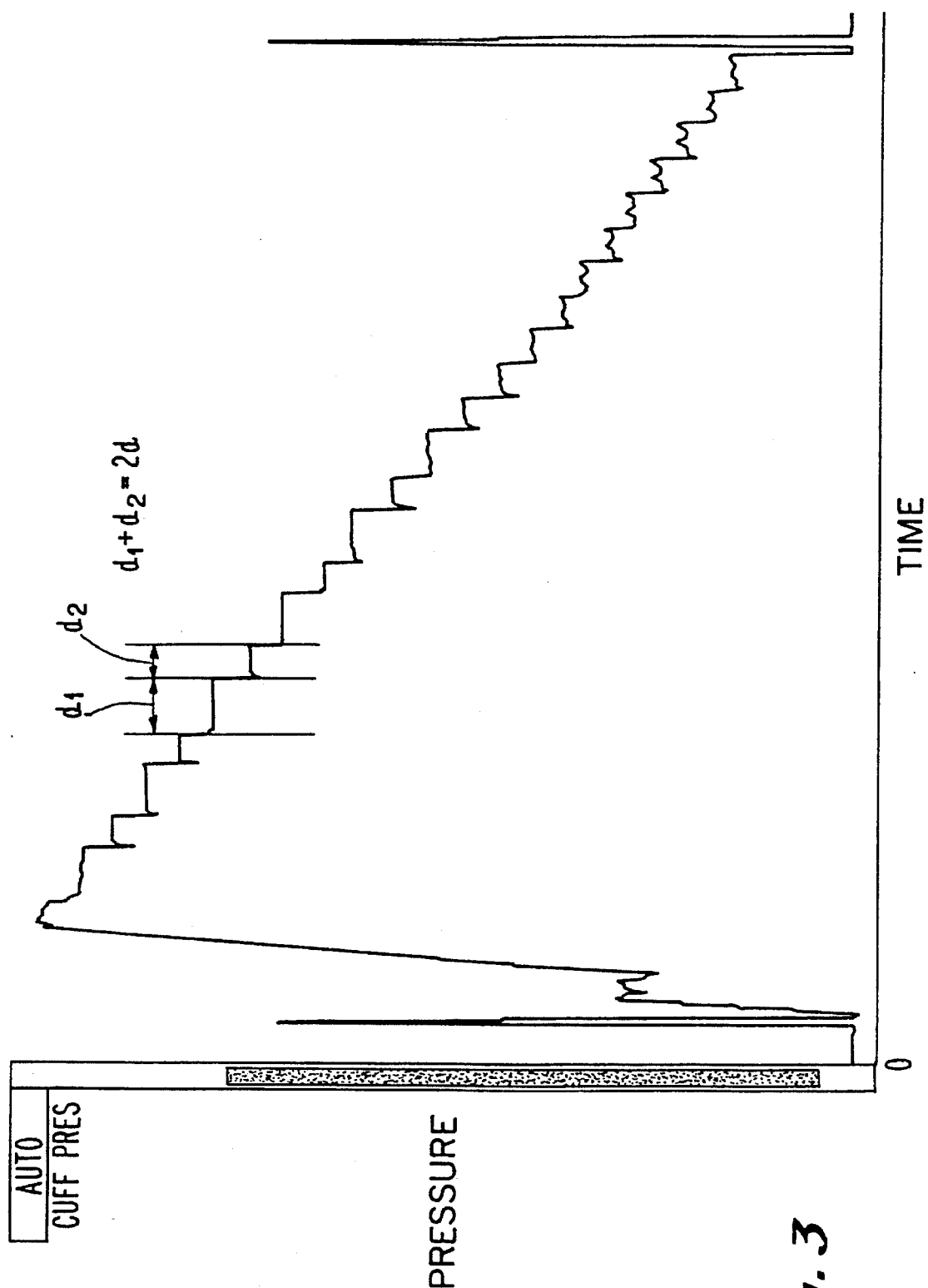
FIG. 3 is a pressure versus time graph illustrating a measuring cycle including step deflation steps of alternating duration in accordance with the invention.

FIG. 3 is a pressure versus time graph for a blood pressure monitor modified in accordance with the principles of the invention so as to eliminate the "synchronization" problem which may occur in conventional blood pressure monitors. As illustrated in FIG. 3, the cuff 101 is inflated to a pressure above systolic pressure and then deflated in equal decrements of about 8 mm Hg for a blood pressure determination as in the prior art. However, in accordance with the invention, the timeout durations of respective deflation steps are alternated at least until such time as oscillatory complexes of sufficient amplitude are detected. As shown in FIG. 3, respective deflation steps have timeout durations of $d_1$ and $d_2$, where $d_1$ does not equal $d_2$, which alternate for respective deflation steps until oscillatory complexes of sufficient amplitude are detected. This approach prevents the noninvasive blood pressure monitor from synchronizing with the heart rate for more than one step. Preferably, $d_1+d_2=2d$ so that the duration of the overall measurement cycle using an alternating deflation technique in accordance with the invention would be the same as the duration of the overall measurement cycle using a conventional deflation technique as illustrated in FIG. 2.

Figure 4:
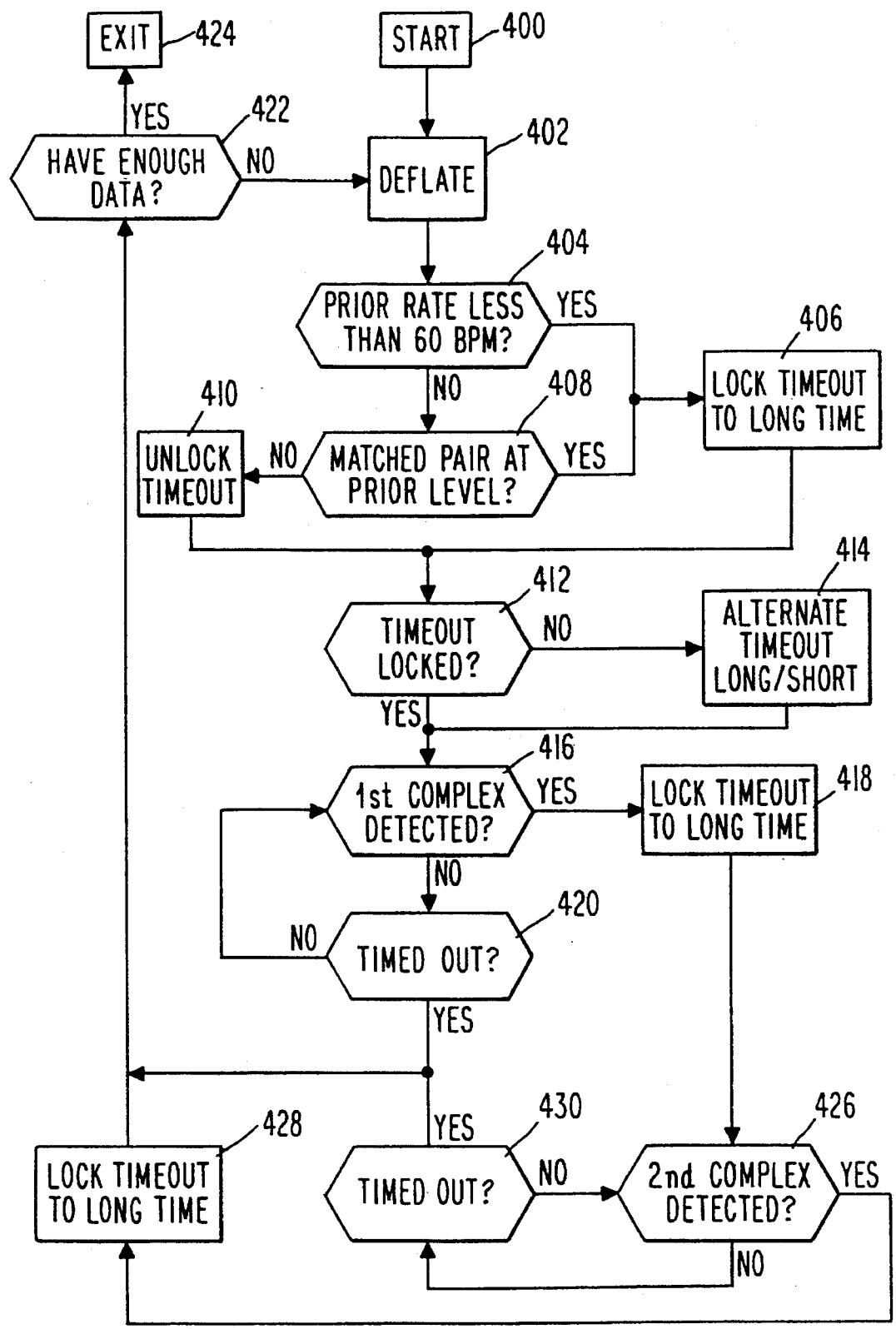
FIG. 4 is a flow chart representing the operation of the apparatus of FIG. 1 under control of a microprocessor programmed to provide alternating step deflation cycles in accordance with the techniques of the invention.

The operation of the present invention will now be described with reference to the flow chart of FIG. 4. Those skilled in the art will appreciate that the flow chart of FIG. 4 is typically implemented in software on microprocessor 108 of FIG. 1 for controlling the step deflation cycle.

At the commencement of the deflation operation at step 400, cuff 101 is deflated at step 402 by pressure increments of a predetermined fixed magnitude, generally about 8 mm Hg per step, by opening deflation valve 102. At step 404, the system checks to determine if the heart rate measured in a previous measurement cycle was less than 60 beats per minute. If so, the timeout duration for the deflation steps is locked to a "long" duration at step 406. However, if the previously measured heart rate is not less than 60 beats per minute, it is determined at step 408 whether a matched pair of oscillatory complexes was detected at the prior step deflation level. If a matched pair of oscillatory complexes was detected at the prior deflation level, the timeout duration for the deflation steps is locked to a "long" duration at step 406. This indicates that the cuff 101 has been deflated to the point that oscillatory complexes may now be detected. However, if it is determined at step 408 that a matched pair of oscillatory complexes was not received at the prior level, and hence that the pressure is either above systolic pressure or well above the mean arterial pressure, the timeout is unlocked at step 410.

If it is determined at step 404 that the patient's heart rate is less than 60 beats per minute or if it is determined at step 408 that a matched pair of oscillatory complexes was detected at the prior deflation level, it is determined at step 412 that the timeout is locked so that the monitor may proceed with conventional oscillatory complex detection procedures. However, if it is determined at step 404 that the patient's heart rate is 60 or more beats per minute and it is determined at step 408 that no matched pair of oscillatory complexes was detected at the prior deflation level, it is determined at step 412 that the timeout is unlocked and that it is thus desirable to alternate the timeout durations in accordance with the techniques of the invention. Thus, if it is determined at step 412 that the timeout is unlocked, the timeout duration is alternated at step 414 and the monitor proceeds to step 416 to determine whether an oscillatory complex is present at the present deflation level. If an oscillatory complex is detected at step 416, the timeout duration is once again locked to the "long" duration at step 418. However, if an oscillatory complex is not detected at step 416, the monitor continues to check for an oscillatory complex until the end of the timeout duration is reached at step 420. At this time, processing proceeds to step 422 where it is determined whether enough data has been collected to determine the patient's blood pressure. If enough data has been collected, the deflation routine is exited at step 424. However, if enough data has not been collected, the cuff 101 is deflated 8 mm Hg to the next deflation step at step 402.

If an oscillatory complex is detected at step 416, the noninvasive blood pressure monitor then searches for a second complex at step 426 so that it may be determined whether the amplitude of the two oscillatory complexes match in accordance with the techniques described by Ramsey et al. in the aforementioned '029 and '034 patents. If a second oscillatory complex is detected at step 426, the timeout duration is again locked to the "long" duration at step 428 and it is determined at step 422 whether enough data has been collected to determine the patient's blood pressure. On the other hand, if a second oscillatory complex is not detected at step 426, the monitor continues to search for the second oscillatory complex until the timeout duration is reached at step 430. It is then determined at step 422 whether enough data has been received to determine the patient's blood pressure and the deflation routine is exited at step 424 as appropriate.

Thus, for typical patients with heart rates greater than 60 beats per minute, the timeout duration is alternated until a matched pair of oscillatory complexes is detected. At that time, the timeout duration is locked to the "long" duration to permit normal processing. However, if the patient's heart rate is less than 60 beats per minute, it is desirable to lock the timeout duration to the "long" duration so that an oscillatory complex can be found at each step. For this to be the case, the "long" duration is preferably chosen to be sufficiently long to permit detection of oscillatory complexes at the lowest expected heart rates.

In accordance with the invention, it is desirable that the time period for the actual deflation of cuff 101 (i.e., the time period during which no measurement is being conducted) be as short as possible to minimize the occurrence of oscillatory complexes during the actual deflation time.

It will be appreciated by those skilled in the art that the foregoing has set forth the presently preferred embodiment of the invention and an illustrative embodiment of the invention but that numerous alternative embodiments are possible without departing from the novel teachings of the invention. For example, those skilled in the art will appreciate that the techniques of the invention may be used for blood pressure monitors in which the pressure is incremented from diastolic as described, for example, in U.S. Pat. No. 4,461,266 to Hood et al. Also, those skilled in the art will appreciate that the techniques of the invention may be used for blood pressure monitors which do not use amplitude matching techniques described by Ramsey to determine whether oscillatory complexes of sufficient quality have been received. In addition, those skilled in the art will appreciate that the techniques of the invention may be expanded to permit multiple, possibly somewhat random, timeout durations for the measurements at respective deflation levels. Accordingly, all such modifications are intended to be included within the scope of the appended claims.

I claim:

1. An automated sphygmomanometer apparatus, comprising:

an inflatable and deflatable pressure cuff;

inflating means operatively coupled to said cuff for selectively applying a medium under pressure to said cuff for inflating and pressurizing said cuff;

cuff pressure sensing means coupled to said cuff for sensing cuff pressure including any blood pressure oscillations therein;

deflating means operatively coupled to said cuff for selectively relieving pressure from said cuff; and control means for measuring a patient's blood pressure from a cuff pressure sensed by said cuff pressure sensing means, said control means controlling said inflating means to inflate said cuff and said deflating means to deflate said cuff during a blood pressure measurement of said patient, said control means instructing said inflating means to inflate said cuff to a predetermined pressure above an estimated systolic pressure of said patient at a beginning of a blood pressure measurement cycle, and said control means instructing said deflating means to deflate said cuff in pressure steps to respective pressure levels for a determination by said control means of the existence and magnitude of blood pressure oscillations in an output of said cuff pressure sensing means at each of said respective pressure levels, whereby during said blood pressure measurement cycle said control means instructs said deflating means to wait a first timeout period for the detection of a blood pressure oscillation at a first pressure level before deflating said cuff to a second pressure level, instructs said deflating means to wait a second timeout period for the detection of a blood pressure oscillation at said second pressure level before deflating said cuff to a third pressure level, and instructs said deflating means to alternate the durations of timeout periods of subsequent pressure levels in said blood pressure measurement cycle between durations lasting for said first and second timeout periods, where said first and second timeout periods of said blood pressure measurement cycle have different durations.

2. An apparatus as in claim 1, wherein said control means instructs said deflating means to select a predetermined timeout period for all pressure levels occurring after the pressure level in said blood pressure measurement cycle at which a blood pressure oscillation of a predetermined quality is detected.

3. An apparatus as in claim 1, wherein said control means further determines the patient's heart rate from said output of said cuff pressure sensing means and, when the patient's heart rate is less than a predetermined rate, said control mean instructs said deflating means to wait a constant timeout period in place of said first and second timeout periods during subsequent searching steps.

4. A method of measuring blood pressure of a patient using an automatic oscillometric blood pressure monitor comprising a pressurized cuff, means for inflating and deflating said cuff to respective blood pressure levels during a blood pressure measurement, and means for measuring arterial pressure oscillation complexes at said respective blood pressure levels through measurement of time varying pressures within said cuff, said method comprising the steps of:

(a) inflating said cuff about an artery of the patient until said cuff is at a first pressure level a predetermined amount above the patient's estimated systolic pressure;

(b) searching for arterial pressure oscillation complexes at said first pressure level for a first timeout period before deflating said cuff from said first pressure level to a second pressure level;

(c) searching for arterial pressure oscillation complexes at said second pressure level for a second timeout period having a duration different from said first timeout period before deflating said cuff from said second pressure level to a subsequent pressure level;

(d) repeating steps (b) and (c) for subsequent pressure levels of said respective blood pressure levels; and (e) measuring the blood pressure of the patient using arterial pressure oscillation complexes found in steps (b)–(d).

5. A method as in claim 4, wherein step (d) comprises the steps of repeating steps (b) and (c) for said subsequent pressure levels until an arterial pressure oscillation complex of a predetermined quality is detected and then conducting all subsequent searching steps for a constant timeout period.

6. A method as in claim 4, comprising the further steps of determining the patient's heart rate and using a constant timeout period in place of said first and second timeout periods during subsequent searching steps when the patient's heart rate is less than a predetermined rate.

* * * * *